(12) United States Patent
Corbalis et al.

(10) Patent No.: US 9,295,878 B2
(45) Date of Patent: *Mar. 29, 2016

(54) INSTRUCTIONAL DISPLAYS AND METHODS FOR AN EXERCISE MACHINE

(71) Applicant: Core Industries, LLC, Irvine, CA (US)

(72) Inventors: Kevin Corbalis, Tustin, CA (US); Jeffrey A Meeks, Orange, CA (US); Michael V Morgan, Laguna Beach, CA (US); John Cook, Ventura, CA (US); Gregory Allen Wallace, Mission Viejo, CA (US); Shatish Mistry, Irvine, CA (US)

(73) Assignee: Core Industries, LLC, Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/322,902

(22) Filed: Jul. 2, 2014

(65) Prior Publication Data

US 2014/0315690 A1 Oct. 23, 2014

Related U.S. Application Data

(63) Continuation of application No. 12/973,691, filed on Dec. 20, 2010, now Pat. No. 8,801,578.

(60) Provisional application No. 61/288,605, filed on Dec. 21, 2009.

(51) Int. Cl.
*A63B 24/00* (2006.01)
*A63B 71/06* (2006.01)
*A63B 22/02* (2006.01)

(52) U.S. Cl.
CPC ............. *A63B 24/0075* (2013.01); *A63B 22/02* (2013.01); *A63B 71/0622* (2013.01); *A63B 2071/0658* (2013.01)

(58) Field of Classification Search
CPC ............... A63B 24/0057; A63B 24/00; A63B 71/0622; A63B 2071/0658; A63B 22/02
USPC ........................... 482/1–9, 900–902; 434/247
See application file for complete search history.

(56) References Cited

U.S. PATENT DOCUMENTS

| | | | |
|---|---|---|---|
| 2007/0042868 A1* | 2/2007 | Fisher et al. | 482/8 |
| 2009/0098981 A1* | 4/2009 | Del Giorno | 482/9 |

* cited by examiner

*Primary Examiner* — Glenn Richman
(74) *Attorney, Agent, or Firm* — Brown IP Law LC; Kerry W. Brown

(57) ABSTRACT

A device for motivating a user of an exercise machine while working out indoors. The device includes an exercise machine, a display connected to the exercise machine, a processor, and a sensor. The processor dynamically creates a workout in response to initialization information. The workout includes a plurality of segments, wherein a segment of the plurality of segments satisfies one or more requirements of the workout. The processor selects one or more video clips that correspond to the segment of the plurality of segments. The sensor communicates information relating to the user to the processor.

20 Claims, 6 Drawing Sheets

INSTRUCTIONAL DISPLAYS AND METHODS FOR AN EXERCISE MACHINE

CROSS-REFERENCE TO RELATED APPLICATIONS

This application is a continuation of U.S. patent application Ser. No. 12/973,691 entitled "Instructional Displays and Methods for Exercise Machine," which was filed on Dec. 20, 2010, which claims benefit under 35 U.S.C. §119(e) to U.S. Provisional Patent Application Ser. No. 61/288,605 filed Dec. 21, 2009, entitled "Instructional Displays And Methods For Exercise Machine," each of which is hereby incorporated by reference.

FIELD

The present invention relates to an exercise apparatus having a display for instructing and/or motivating a user during a workout routine.

BACKGROUND

Trends towards physical fitness awareness have led to an increase in the number of individuals exercising to keep physically fit. In order to stay in shape, exercise enthusiasts can generally perform exercises such as running or biking either outside on paths or trails, or can perform them inside on a machine. A machine allows an enthusiast to perform the exercise indoors with full ranges of motion without requiring the large amount of space that exercising outdoors demands.

SUMMARY

The present disclosure provides for a motivating and instructional user interface or display for indoor exercise machines. A virtual coach or other encouraging stimulus provides key motivation for users of indoor exercise machines which may suffer from the lack of change of scenery and other drawbacks of indoor machines. In an embodiment, a device for motivating an exercise enthusiast while working out indoors is provided including an exercise machine for providing the exercise enthusiast a stationary apparatus to perform a predetermined exercise type. In an embodiment, a display is connected to the exercise machine and a memory is in electrical communication with the display, where the memory stores at least one video clip.

In another embodiment, the memory includes at least one exercise segment associated with the at least one video clip. Also, the display may be configured to receive input from the exercise enthusiast and the video clip may be configured to include a virtual coach. In one embodiment, the virtual coach may be a pre-recorded video clip of a live instructor, an animated figure, a series of text messages, or may provide instructions on aspects of the associated exercise segment. In another embodiment, the input received by the display is information associated with the selection of an exercise program associated with the at least one exercise segment.

In another embodiment, a method of displaying an instructional image to an exercise enthusiast is provided including receiving an input relating to an exercise program and displaying a video clip associated with the exercise program on a display attached to an exercise machine. In an embodiment the input may be associated with an exercise segment that is associated with the video clip.

In another embodiment, a device for providing instructional support to an exercise enthusiast training on an indoor exercise machine is provided with a user input device for inputting information associated with a desired workout program. In an embodiment, a memory may be in electrical communication with the user input device for storing at least one exercise segment. In some embodiments, at least one video clip associated with the at least one exercise segment is provided and a display for displaying the at least one video clip associated with the at least open segment is provided.

In an embodiment, the device includes a processor for coordinating the display and processing of the input commands. In a further embodiment, the display is connected to an exercise machine.

For purposes of summarizing the disclosure, certain aspects, advantages and novel features have been described herein. Of course, it is to be understood that not necessarily all such aspects, advantages or features will be embodied in any particular embodiment of the disclosure.

DETAILED DESCRIPTION

Figure 1A:
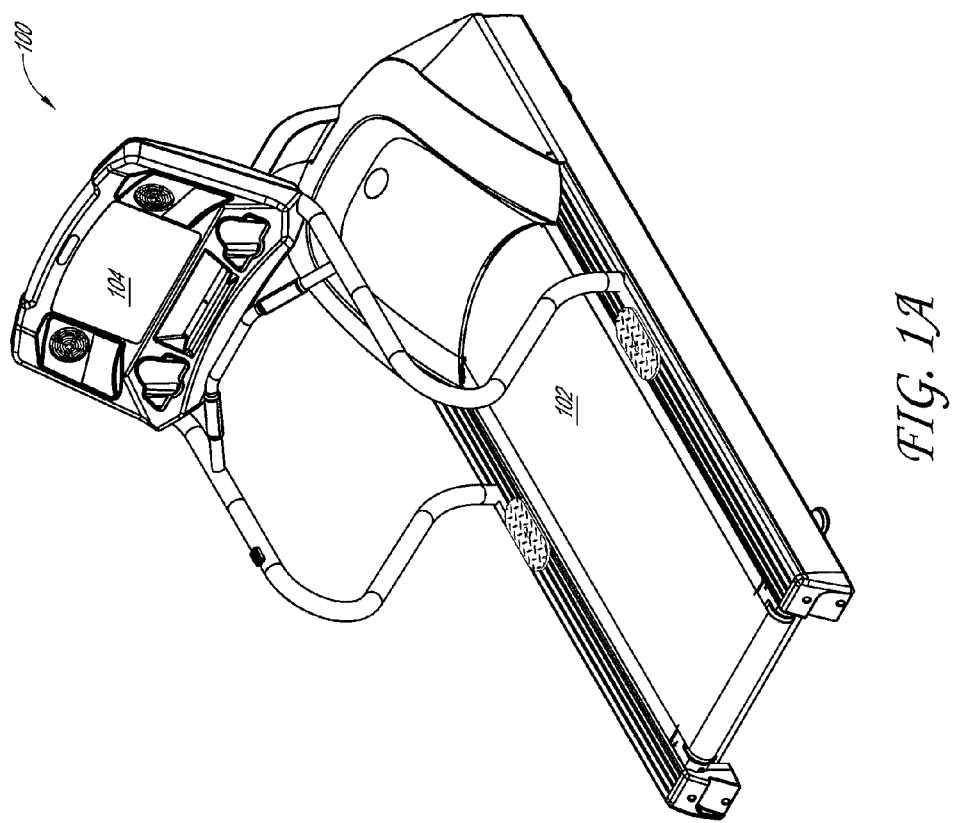
FIG. 1A illustrates a perspective view of a treadmill exercise machine according to certain embodiments of the invention.

Stationary exercise machines, such as treadmills, steppers, and the like have become popular choices for exercise enthusiasts who are unable to engage in outdoor exercise or who want to avoid the attendant inconvenience of outdoor exercise. Working out indoors allows the enthusiast to exercise regardless of the weather and avoids the need for long paths or routes to follow.

Indoor exercise, however, does have disadvantages. For example, users of stationary exercise machines generally experience the same environment each time they perform their exercise routines. A user often goes to the same indoor workout facility and exercises on the same machine or group of machines. The surrounding "scenery" remains generally the same from day to day. Furthermore, users of stationary exercise machines often perform their exercise routines alone without interaction from others.

To address at least some of the attendant drawbacks of indoor exercise, several conventional exercise machines include user interfaces for motivating the user during his or her exercise routine. For example, certain treadmills and/or steppers include a motivational track comprised of multiple light emitting diodes (LEDs) arranged in a substantially oval shape. As the user progresses through the workout, the display updates the track display to show the user his or her progress and/or to motivate the user to complete the exercise routine. Other users participate in exercise classes in which a live instructor leads a group in particular exercise routines.

Certain exercisers also engage in non-exercise related activities, such as watching television or movies, playing video games, or listening to music to help pass time during an exercise routine. Such activities, however, are relatively disconnected from the exercise itself, and can even promote poor exercise form.

In view of the drawbacks discussed above, what is needed is an exercise machine that provides a user with a variety of instructional exercise routines and/or displays for assisting and/or motivating a user during a workout.

In certain embodiments of the invention, an exercise machine provides a user with a customized instructional video display to "coach" the user through a selected workout program. For example, the display may comprise a plurality of video clips having a virtual coach that instructs and motivates a user during multiple segments of a workout routine. In certain embodiments, the exercise segments are selected from a plurality of available segments and/or randomized to provide the user with a different workout each time the user exercises, even if the same workout parameters are selected. Each of the instructional video clips can also be selected (e.g., randomly drawn) from one or more pools of video clips that are associated with the determined workout segments.

The features of the systems and methods will now be described with reference to the drawings summarized above. The drawings, associated descriptions, and specific implementation are provided to illustrate embodiments of the invention and not to limit the scope of the disclosure.

FIG. 1A illustrates an exercise machine 100 comprising a treadmill according to an embodiment of the invention. For instance, the exercise machine 100 can comprise a microprocessor-controlled exercise device affording a user an aerobic workout, such as, for example, walking, jogging or running over simulated terrain conditions at various speeds and incline levels.

Figure 1B:
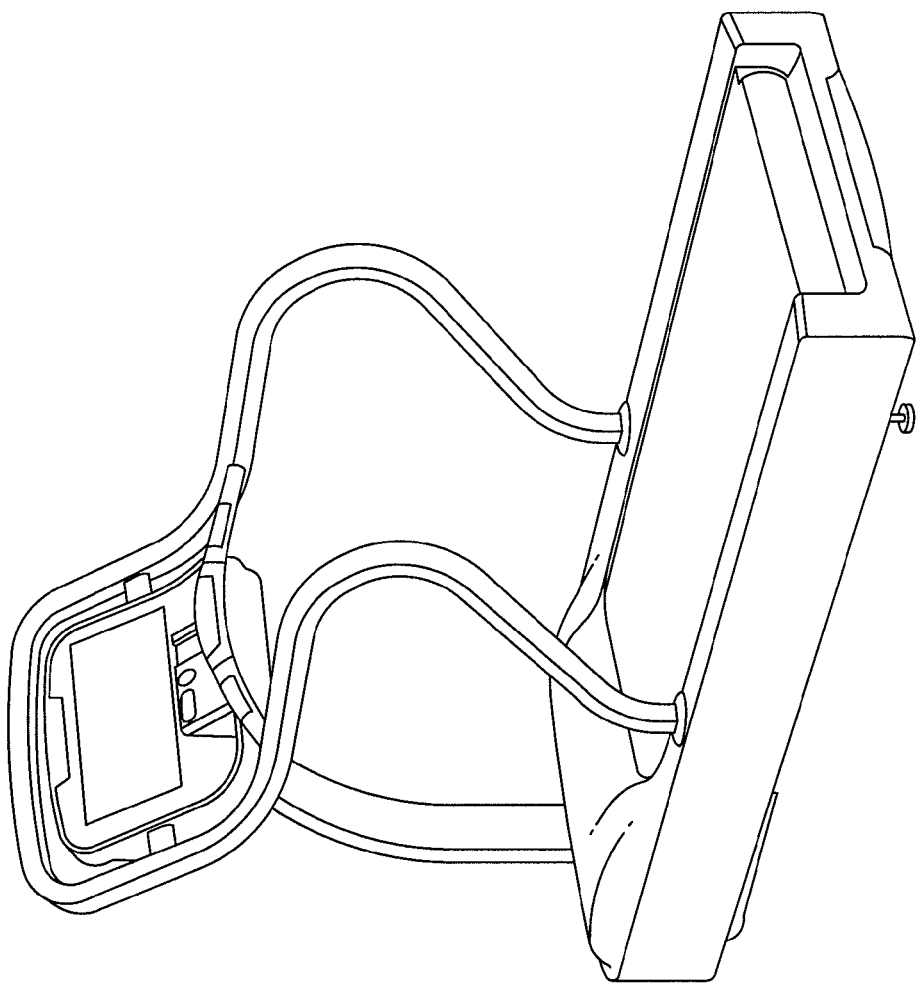
FIG. 1B illustrates a perspective view of another treadmill exercise machine usable with embodiments of the invention.
Figure 1C:
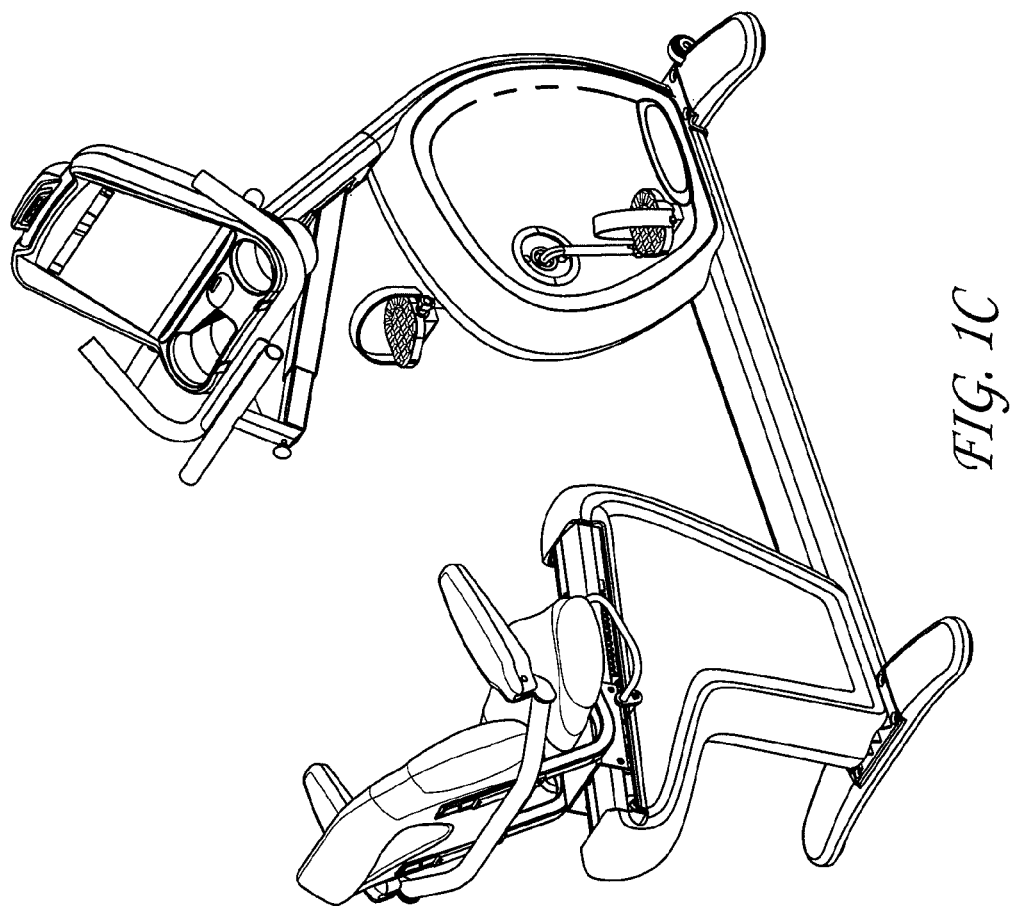
FIG. 1C illustrates a perspective view of a recumbent bicycle exercise machine usable with embodiments of the invention.

In yet other embodiments, the exercise machine 100 can provide a workout including biking, climbing, skiing, lifting or the like. For instance, the exercise machine 100 may advantageously comprise a stepper, spinner, stairclimber, natural runner, stationary bicycle, elliptical machine, rowing machine, climbing machine, skiing machine, skating machine and the like. For instance, FIGS. 1B and 1C illustrate, respectively, another treadmill exercise machine and a recumbent bicycle machine usable with embodiments of the invention.

As shown in FIG. 1A, the exercise machine 100 comprises an exercise assembly 102 having mechanical mechanisms that interact with the user to provide the user with exercise. For example, in the embodiment of a treadmill, the exercise assembly 102 includes an endless belt extended over a support surface and rotated by a motor controlled by a controller board in a fashion which allows a user standing thereon to walk, jog, run or the like. However, a skill artisan will recognize from the disclosure herein that other exercise assemblies may provide exercise to the user without electronic drive components, such as, for example, a stationary bike, a climbing machine, a striding elliptical machine, or the like.

Furthermore, the exercise machine 100 may be advantageously self-contained such that the exercise machine 100 provides substantiality all of its own electrical power for operation through the exerciser's input. In other embodiments, the exercise machine 100 may operate at least partially on an AC power supply and/or one or more batteries.

The exercise machine 100 further comprises a display 104 that provides feedback on various workout parameters, including, for example, current and aggregate data related to the current or historical workout. In certain embodiments, the display 104 also provides for user input, such as, for example, the selection of a particular workout routine, a resistance level, and other user-related data. In certain preferred embodiments, the display 104 further provides a virtual coach for instructing and/or motivating a user during a unique workout routine.

Figure 2:
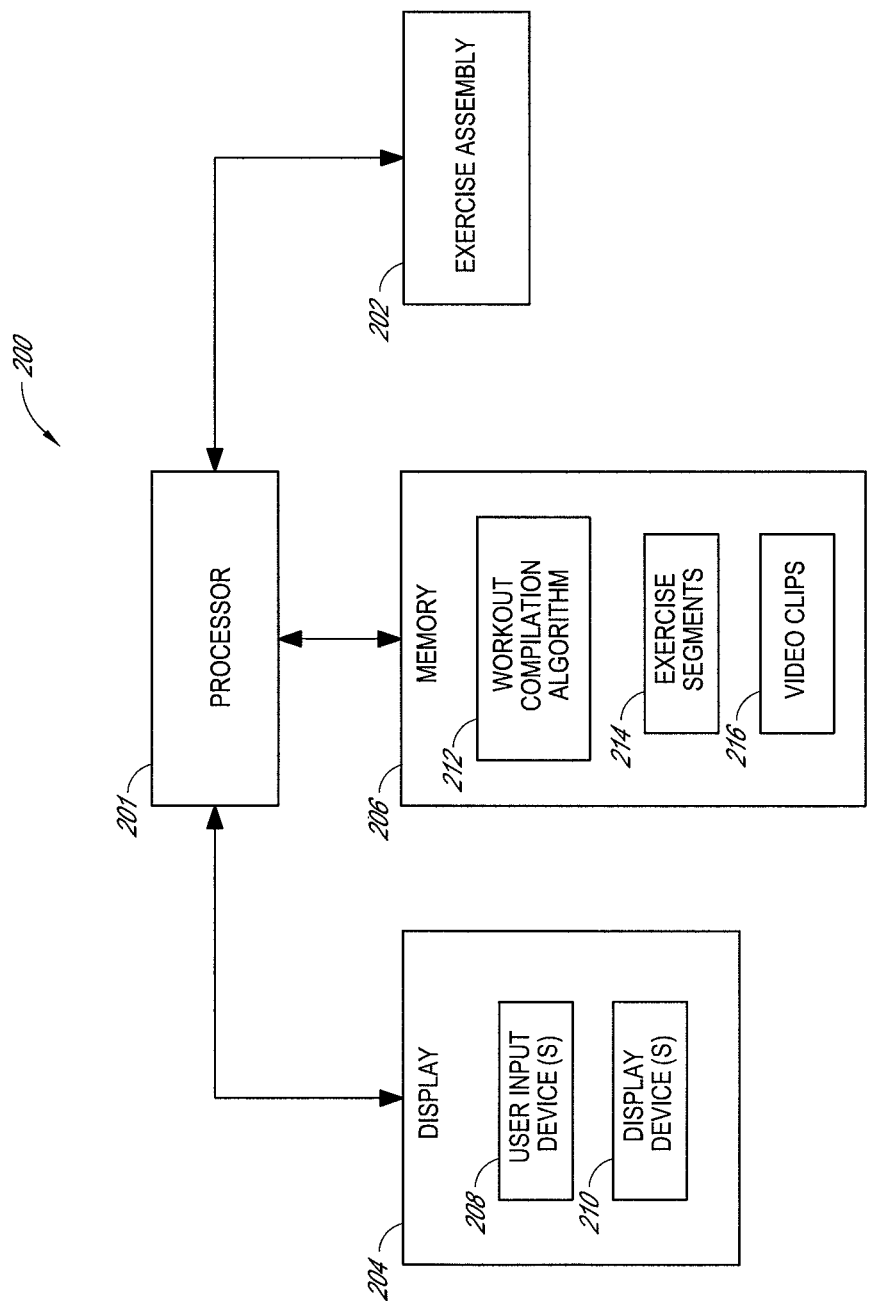
FIG. 2 illustrates a block diagram of an exemplary embodiment of a control system of the treadmill exercise machine of FIG. 1A.

FIG. 2 illustrates a block diagram of an exemplary embodiment of a control system 200 usable by an exercise machine, such as the exercise machine 100 of FIG. 1A. As shown, the control system 200 comprises a processor 201 that communicates with an exercise assembly 202, a display 204 and a memory 206.

In general, the processor 201 receives user input through the display 204 and/or information from one or more sensors relating to the user's operation of the exercise machine 100. The processor 201 may also access and/or store information, such as data and/or executable instructions, in the memory 206. The processor 201 is further capable of generating signals for adjusting the operation of the exercise assembly 202 and/or controlling the output of the display 204.

The display 204 can have any suitable construction known to an artisan to display information and/or to instruct and/or motivate the user during a workout routine, provide current or historical exercise information, illustrate progress of the user's workout and the like. As illustrated in FIG. 2, the processor 201 communicates with the display 204 to receive user input through at least one user input device 208 and to provide user output through at least one display device 210.

The user may input information, such as, for example, initialization data or resistance level selections, through the user input device 208. Such initialization data may include, for instance, the weight, age, and/or sex of the user, the workout program selection(s), other demographic information, combinations of the same or the like. A skilled artisan will recognize from the disclosure herein a wide variety of other data usable to calculate exercise progress or parameters, including a wide variety of fitness parameters, physiological parameters and the like. The user input device 208 may comprise, for example, buttons, keys, a heart rate monitor, a touch screen, a personal digital assistant (PDA), cellular phone or the like. Moreover, an artisan will recognize from the disclosure herein a wide variety of devices usable to collect user input.

Furthermore, the display device 210 of the display 204 advantageously provides the user with information relating to his or her exercise routine, such as for example, the selected workout program, the user's exercise pace, the time expended or remaining in the workout routine, the simulated distance traveled, the user's heart rate, combinations of the same or the like. The display device 210 also comprises, for example, a video screen for providing a virtual coach to instruct and/or motivate the user through a series of exercise segments during the user's workout routine. In yet other embodiments, the display 204 can comprise LED matrices, a 7-segment liquid crystal display (LCD), a motivational track, an external display, combinations of the same and/or any other device or apparatus that is used to display information to a user.

In certain embodiments, the processor 201 communicates with the memory 206 to retrieve and/or to store data and/or program instructions for software and/or hardware. As shown, the memory 206 stores a workout compilation algorithm 212, such as software instructions, rules or policies, for selecting and/or ordering one or more exercise segments 214 in constructing a workout routine for the user.

The memory 206 also includes a plurality of pre-recorded video clips 216 associated with the exercise segments 214 that can be displayed to the user during the workout routine.

In certain embodiments, the video clips 216 include an instructor, a virtual "coach," that guides the user through a particular exercise segment. For instance, the virtual coach can instruct and/or provide a visual example to a user of one or more of the following parameters during the exercise segment: intensity or speed of the exercise, incline of the exercise assembly 202, resistance level, duration of a particular exercise, posture or exercise form guidance (e.g., correct posture, hand/leg positioning or movement, warm-up or cool-down movements, combinations of the same or the like.

In certain embodiments, each video clip 216 is associated with a single exercise segment 214. In yet other embodiments, multiple video clips 216 can be displayed during one exercise segment 214, or multiple exercise segments 214 can be associated with a single video clip 216. Moreover, in certain embodiments the video clips 216 are each of the same duration (e.g., five minutes). In yet other embodiments, the video clips 216 are of varying lengths, such as for example, from one to ten minutes.

In some embodiments, the user may select different workout destinations that correspond to different backgrounds for the video clip 216. In some embodiments, the virtual coach may give different feedback for different exercise segments 214 depending on the chosen background. For example, if a mountain background is chosen and the exercise segment 214 is going uphill, the virtual coach may give encouragement relating to reaching the peak of the mountain. Also, a variety of other backgrounds may be chosen such as, forests, deserts, valleys, marathons, racing other virtual workout figures, or a paddle boat for a stationary bike.

In certain embodiments, the processor 201 and the memory 206 are housed within the display 204. In other embodiments of the invention, the processor 201 and/or the memory 206 are located within or near the exercise assembly 202, such as on a load control board, or within or on other locations on the exercise machine. In yet other embodiments, the processor 201 and/or memory 206 are located external to, or remote to, the exercise machine 100. In yet other embodiments of the invention, a portion of the processor 201 may be housed in the display 204, and another portion of the processor 201 may be located within the exercise assembly 202.

As also will be understood by a skilled artisan from the disclosure herein, the memory 206 may comprise random access memory (RAM), ROM, on-chip or off-chip memory, cache memory, or other more static memory such as magnetic or optical disk memory. The memory 206 may also access and/or interact with CD-ROM data, PDAs, cellular phones, laptops, portable computing systems, wired and/or wireless networks, combinations of the same or the like.

Although the control system 200 is disclosed with reference to particular embodiments, a skilled artisan will recognize from the disclosure herein a wide number of alternatives for the processor 201, the exercise assembly 202, the memory 206, and/or the display 204. For example, the processor 201 may comprise an application-specific integrated circuit (ASIC) or one or more modules configured to execute on one or more processors. The modules may comprise, but are not limited to, any of the following: hardware or software components such as software object-oriented software components, class components and task components, processes, methods, functions, attributes, procedures, subroutines, segments of program code, drivers, firmware, microcode, applications, algorithms, techniques, programs, circuitry, data, databases, data structures, tables, arrays, variables, or the like.

Figure 3:
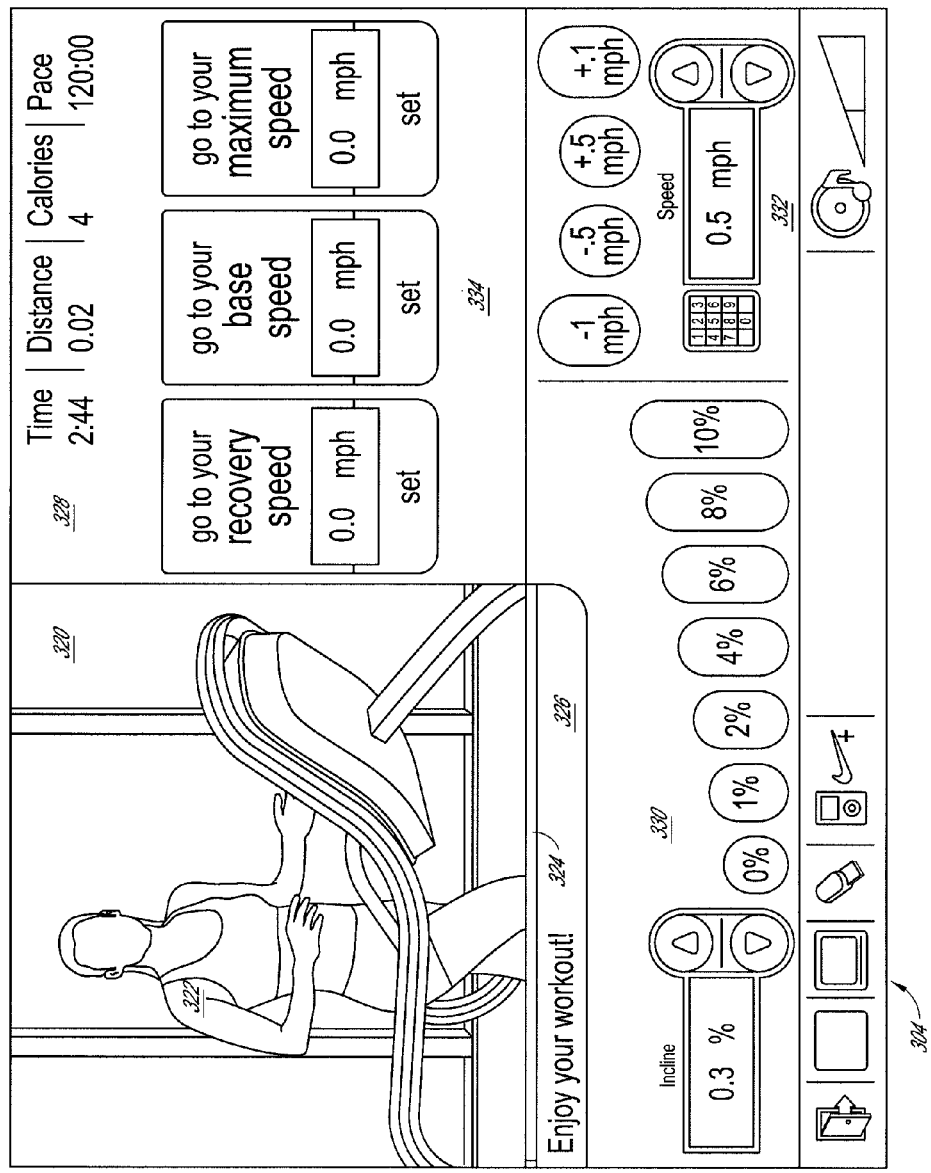
FIG. 3 illustrates an exemplary embodiment of an instructional display of the treadmill exercise machine of FIG. 1A.

FIG. 3 illustrates an exemplary embodiment of an electronic display 304 having an instructional user interface usable by the exercise machine 100 of FIG. 1A. As shown, the display 304 includes an instructional view window 320 with a virtual coach 322, an exercise segment time bar 324, a message window 326 and workout statistics 328 that are capable of providing workout feedback to a user. In addition, FIG. 3 shows the display 304 comprising an incline control section 330, a speed control section 332 and a quick input section 334, which are each capable of receiving input from the user for dynamically adjusting parameters of the workout routine.

In certain embodiments, the virtual coach 322 of the window 320 instructs and/or provides motivation to a user throughout a workout routine. For instance, the window 320 may display a plurality of successive video clips 216 with the virtual coach that correspond to specific selected exercise segments 214 of the workout routine. In certain embodiments, the virtual coach 322 can comprise an individual (e.g., a prerecorded video image of a live individual). In yet other embodiments, the virtual coach 324 can comprise an animated character, an avatar, or the like. In yet other embodiments, the window 320 can also include personalized background images that are selected based on the particular user workout (e.g., background showing mountainous terrain when the user is exercising on an incline), user preferences, or the like.

The exercise segment time bar 324 displays how much time has elapsed and/or is remaining in an exercise segment 214 that corresponds to the video clip displayed through the window 320. In yet other embodiments, the bar 324 can display how much time has elapsed and/or is remaining in the current video clip 216.

The message window 326 displays to the user informational messages, instructions during program initialization, feedback during the workout routine, and/or summaries of workout data when the user completes the workout. The workout statistics section 328 provides current and/or aggregate data related to the current workout of the user. For example, the workout statistics section 328 can include one or more of the following: total time remaining in a workout, total time elapsed in the workout, total distance traveled, caloric expenditure, current speed/pace, combinations of the same or the like.

FIG. 3 further illustrates the display 304 having several input portions for receiving selections of a user. For example, the display 304 includes an incline control section 330 for manually controlling an incline of the exercise machine 100 (e.g., the exercise assembly 102). The speed control section 332 allows a user to manually adjust a speed of the exercise assembly 102. The quick input section 334 provides oversize touch screen buttons for easy access by a user to set and/or select one of three predetermined speed (i.e., a "recovery" speed, a "base" speed and a "maximum" speed). The oversize buttons are especially advantageous for facilitating quick user speed selections during the workout routine since it can be difficult, at certain times, to input data through buttons with a smaller surface area during exercise movements.

Although the display 304 has been described with reference to particular embodiments, it will be appreciated that other embodiments of the invention can include more or fewer controls or features that the illustrated display 304. For instance, in certain embodiments, the display 304 can comprise a resistance selection section, an audio/video control portion or the like.

Figure 4:
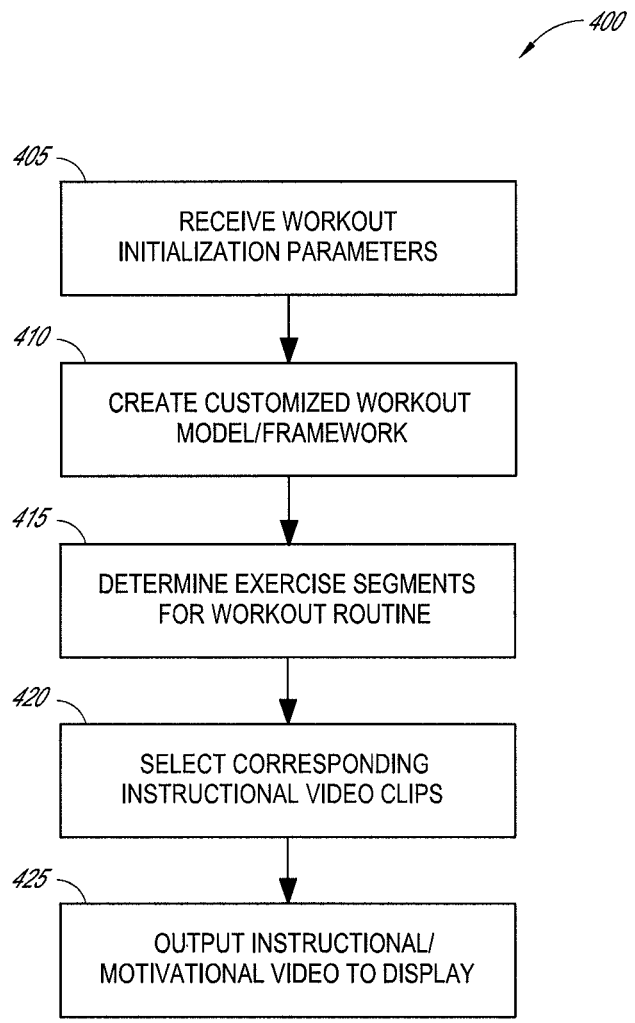
FIG. 4 illustrates a simplified flowchart of an exemplary embodiment of a workout program process executable by the control system of FIG. 2.

FIG. 4 illustrates a flowchart of an exemplary embodiment of a workout program process 400. In certain embodiments, the process 400 is executed by the electronic control system 200 depicted in FIG. 2 to coach a user through an aerobic exercise on a stationary exercise machine, such as the exercise machine 100 depicted in FIG. 1A.

In general, the process 400 is capable of generating customized workout routines for a user based on initial workout parameters. In certain embodiments, the customized workout is built with a plurality of individual exercise segments 214 drawn from a pool of available segments such that a user does not consistently experience the same workout routine each time the user exercises.

As shown, the process 400 begins with Block 405 where the processor 201 receives through one of the user input devices 208 on the display 204 a user selection of a workout routine. For example, a user of the exercise machine may input initialization information indicative of one or more of the following workout parameters: a preselected workout type (e.g., fat burning, strength building, cardio, endurance), the weight of the user, desired heart rate range, the age of the user, the user's exercise experience (e.g., beginner, intermediate, expert), desired caloric expenditure, workout length, simulated terrain type (e.g., level, hills, mixed, random), combinations of the same or the like. In other embodiments of the invention, the processor 201 receives one or more of the initialization parameters from the memory 308, from PDAs, cellular phones, or other separate computing devices.

At Block 410, the processor 201 generates a personalized workout framework or model based on the initialization parameters received in Block 405. In certain embodiments, the processor 201 executes the workout compilation algorithm 212 to determine which types of exercise segments 214 are needed to compile an exercise routine that satisfies the requirements of the initialization parameters. For instance, the algorithm 212 can determine based on one or more predetermined criteria or rules that an appropriate workout routine for the user must contain at least a particular number of one or more types of exercise segments 214 (e.g., a hill segment, a "sprint" segment, a recovery segment, a pyramid segment, an endurance segment, combinations of the same or the like). In yet other embodiments of the invention, the workout compilation algorithm 212 can select one or more workout models from a pool of pre-generated models.

At Block 415, the processor 201 dynamically generates a customized exercise routine based on the workout model constructed in Block 410. In certain embodiments, the algorithm 212 selects a plurality of exercise segments 214 that satisfy the requirements of the workout model. For instance, the processor 201 can randomly select particular exercise segments from one or more pools of available exercise segments 214 to compile the exercise routine. In certain further embodiments, the selected exercise segments 214 can be further randomized for their order of execution during the compiled exercise routine. In yet other embodiments of the invention, each workout model is associated with a predetermined arrangement of exercise segments 214.

At Block 420, the processor 201 selects instructional video clips 216 that are associated with the selected exercise segments 214. As discussed above, in certain embodiments, each exercise segment 214 can be associated with a pool of appropriate instructional video clips 216. Thus, for each determined exercise segment 214, the processor 201 can randomly select from the appropriate pool (e.g., of tens or hundreds of video clips), a video clip 216 to display to the user during the workout routine.

In certain embodiments, Block 420 is performed prior to the user commencing exercise. In yet other embodiments, the selection of the subsequent exercise segment 214 and/or instructional video clip 216 is performed dynamically, in real-time, during the user's workout routine.

At Block 425, the processor 201 displays the instructional video clips to the user via the display 204 (e.g., the window 320), during the workout routine of the user. It will be appreciated that the workout program process 400 is capable of compiling hundreds or thousands of customized workout programs and instructional video sets based on the received initialization parameters. Thus, even if a user inputs the same initialization parameters during successive workouts, the process 400 can advantageously generate different workout routines and/or instructional video sequences so that the user does not experience the same workout routine or instructional video sequence between any two workout routines (or any two workout routines during a particular time period).

Although the workout program process 400 has been disclosed with reference to particular embodiments, a skilled artisan will recognize from the disclosure herein a wide variety of acts or blocks that may be included in the process 400. For example, in certain embodiments, the control system 200 can monitor the exercise of the user via one or more sensors and dynamically select appropriate exercise segments 214 for a workout routine. For instance, the control system 200 can monitor a heart rate, an exercise pace, caloric expenditures or the like and intelligently control the selection of appropriate exercise segments and/or instructional video clips. In one example, if the heart rate of a user during exercise exceeds a particular threshold, the algorithm can select a less intensive (e.g., slower pace or decrease in the incline) exercise segment and/or an instructional video segment that guides the user in reducing the intensity of the exercise. In yet other embodiments, the user can select from a plurality of virtual coaches.

In yet further embodiments, the processor 201 can automatically adjust one or more workout parameters during the workout routine of the user to be consistent with a selected exercise segment. For instance, the processor 201 can automatically adjust an incline, a resistive load, a speed, or the like of the exercise assembly 202 to match the workout requirements of the particular exercise segment 214. In further embodiments, the processor 201 can automatically control a fan device, background music or the like to enhance the user's workout experience.

A skilled artisan will also recognize from the disclosure herein that the blocks described with respect to the foregoing process 400 are not limited to any particular sequence, and the blocks relating thereto can be performed in other sequences that are appropriate. For example, described blocks may be performed in an order other than that specifically disclosed or may be executed in parallel, or multiple blocks may be combined in a single block. In addition, not all blocks need to be executed or additional blocks may be included without departing from the scope of the invention.

Furthermore, a skilled artisan will recognize from the disclosure herein that one or more functions of embodiments of the exercise machine may be implemented, at least in part, in software that is executable on one or more processors. For instance, a software program executing on a processor of the exercise machine may perform one or more of the following: monitor a progress of an individual during one or more exercise machines, track and/or analyze trend data relating to one or more users' exercise routines; control one or more display graphics, combinations of the same or the like.

In further embodiments, a software program may export data relating to the user's performance during one or more exercise routines. The exported data may include information related to, for example, caloric expenditure, heart rate, distance traveled or climbed, workout program selection and/or completion, exercise speed, length of time, combinations of the same and the like. For instance, such exported data may be used by a therapist to evaluate a user's performance and/or to develop a workout schedule for the user. The user may use such data to generate a summary of his or her exercise performance, to compare his or her performance with previous performances or against performances of another user, or the like. Furthermore, the exported data may be transferred to a PDA, cellular phone or other computing device for further processing and/or analyzing.

While certain embodiments of the inventions have been described, these embodiments have been presented by way of example only, and are not intended to limit the scope of the disclosure. It must be understood that in the context of the present invention, exercise machines described herein are to be construed as any type of exercise equipment or device whereby a human exerciser may translate exercise of any one of the limbs or portion of the body into a motion which is translated into a motive force capable of driving a load. Thus, an exercise machine may include any type of exercise or work load machine now known or later devised, such as described in U.S. Pat. No. 7,070,542, issued Jul. 4, 2006; U.S. Pat. No. 7,585,251, issued Sep. 8, 2009; U.S. Patent Application Publication No. 2006-0003872 A1, published Jan. 5, 2006; U.S. Patent Application Publication No. 2007-0197345 A1, published Aug. 23, 2007; and U.S. Patent Application Publication No. 2006-0189439 A1, published Aug. 24, 2006, each of which is hereby incorporated herein by reference in its entirety.

Systems and modules described herein may comprise software, firmware, hardware, or any combination(s) of software, firmware, or hardware suitable for the purposes described herein. Software and other modules may reside on servers, workstations, personal computers, computerized tablets, PDAs, and other devices suitable for the purposes described herein. Software and other modules may be accessible via local memory, via a network, via a browser, or via other means suitable for the purposes described herein. Data structures described herein may comprise computer files, variables, programming arrays, programming structures, or any electronic information storage schemes or methods, or any combinations thereof, suitable for the purposes described herein.

Embodiments of the invention are also described above with reference to flowchart illustrations and/or block diagrams of methods, apparatus (systems) and computer program products. It will be understood that each block of the flowchart illustrations and/or block diagrams, and combinations of blocks in the flowchart illustrations and/or block diagrams, may be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the acts specified in the flowchart and/or block diagram block or blocks.

These computer program instructions may also be stored in a computer-readable memory that can direct a computer or other programmable data processing apparatus to operate in a particular manner, such that the instructions stored in the computer-readable memory produce an article of manufacture including instruction means which implement the acts specified in the flowchart and/or block diagram block or blocks. The computer program instructions may also be loaded onto a computer or other programmable data processing apparatus to cause a series of operations to be performed on the computer or other programmable apparatus to produce a computer implemented process such that the instructions, which execute on the computer or other programmable apparatus, provide steps for implementing the acts specified in the flowchart and/or block diagram block or blocks.

Indeed, the novel methods and systems described herein may be embodied in a variety of other forms; furthermore, various omissions, substitutions and changes in the form of the methods and systems described herein may be made without departing from the spirit of the inventions.

What is claimed is:

1. A device for motivating a user of an exercise machine while working out indoors, the device comprising:
   an exercise machine for providing the user a stationary apparatus to perform a predetermined exercise type;
   a display connected to the exercise machine;
   a memory in electrical communication with the display, the memory storing at least one video clip;
   a processor to:
      dynamically create a workout in response to initialization information, the workout comprising a plurality of segments, wherein a segment of the plurality of segments satisfies one or more requirements of the workout; and
      select one or more video clips that correspond to the segment of the plurality of segments; and
   a sensor to communicate information relating to the user to the processor.

2. The device of claim 1 wherein the processor creates the workout in response to the information communicated by the sensor.

3. The device of claim 1 wherein the processor selects a segment of the plurality of segments in response to the information communicated by the sensor.

4. The device of claim 1 wherein the processor selects a video clip of the one or more video clips in response to the information communicated by the sensor.

5. The device of claim 1 wherein the sensor senses information relating to the user.

6. The device of claim 1 wherein the information relating to the user comprises a heart rate of the user.

7. The device of claim 1 wherein the information relating to the user comprises a blood pressure of the user.

8. The device of claim 1 wherein the information relating to the user comprises a breathing rate of the user.

9. The device of claim 1 wherein the information relating to the user comprises a cadence of the user.

10. A method of displaying an instructional image to user, the method comprising:
   receiving an input of initialization information relating to an exercise program;
   receiving an input of information relating to the user from a sensor;
   dynamically creating a workout in response to the initialization information, the workout comprising a plurality of segments, wherein a segment of the plurality of segments satisfies one or more requirements of the workout;
   selecting a plurality of video clips wherein each video clip of the plurality of video clips corresponds to one or more segments of the plurality of segments; and
   displaying a the plurality of video clips associated with the exercise program on a display attached to an exercise machine.

11. The method of claim 10, wherein the sensor comprises a heart rate monitor.

12. The method of claim 10, wherein the sensor comprises an electrocardiogram machine.

13. The method of claim 10, wherein the sensor comprises a pulse oximeter.

14. The method of claim 10, wherein the sensor comprises a camera.

15. A device for providing instructional support to user training on an indoor exercise machine comprising:
   a user input device for inputting initialization information associated with a desired workout program;
   a sensor to monitor the exercise of the user and produce user data;
   a memory in electrical communication with the user input device for storing at least one exercise segment;
   a processor to:
      dynamically create a workout in response to the initialization information, the workout comprising a plurality of segments, wherein each segment of the plurality of segments satisfies one or more requirements of the workout; and
      order the plurality of segments into a predetermined order associated with the workout program;
      select a plurality of video clips wherein each video clip of the plurality of video clips corresponds to one or more segments of the plurality of segments;
      order the video clips for display in response to the order of corresponding segments; and
   a display connected to an exercise machine for displaying the plurality of video clips.

16. The device of claim 15, wherein the processor dynamically modifies the workout in response to user data collected by the sensor.

17. The device of claim 16, wherein the processor selects an alternative segment to replace a segment of the plurality of segments.

18. The device of claim 16, wherein the processor selects an alternative video clip to replace a video clip of the plurality of video clips.

19. The device of claim 16, wherein the processor adjusts a workout parameter relating to operation of the indoor exercise machine in response to user data exceeding a predetermined threshold.

20. The device of claim 16, wherein the workout parameter is selected from the group consisting of an incline, a resistive load, and a speed associated with the indoor exercise machine.

* * * * *